United States Patent [19]

McLoughlin et al.

[11] 4,124,709
[45] Nov. 7, 1978

[54] ANOREXIANTS

[75] Inventors: Bernard J. McLoughlin; Allen J. Guildford, both of Macclesfield, England

[73] Assignee: Imperial Chemical Industries Limited, London, England

[21] Appl. No.: 815,846

[22] Filed: Jul. 14, 1977

[30] Foreign Application Priority Data

Jul. 14, 1976 [GB] United Kingdom ............... 29297/76

[51] Int. Cl.$^2$ .......................... A01N 9/00; A01N 9/22
[52] U.S. Cl. ................................................. 424/248.4
[58] Field of Search ...................... 424/248.4; 544/106

[56] References Cited

U.S. PATENT DOCUMENTS

| 3,806,595 | 4/1974 | Jagger et al. ................... 424/248.58 |
| 4,010,266 | 3/1977 | McLoughlin et al. ............ 424/248.4 |
| 4,049,808 | 9/1977 | McLoughlin et al. ............ 424/248.4 |

OTHER PUBLICATIONS

The Pharmacological Basis of Therapeutics - 1966 pp. 515-517.

*Primary Examiner*—Albert T. Meyers
*Assistant Examiner*—D. W. Robinson
*Attorney, Agent, or Firm*—Cushman, Darby & Cushman

[57] ABSTRACT

A method of producing anorexia in warm-blooded animals which comprises administering racemic 2-(β-phenyl-trans-vinyl)morpholine or the (2R) isomer thereof.

6 Claims, No Drawings

ANOREXIANTS

This invention relates to anorexiants, and in particular it relates to a method of producing anorexia in warm-blooded animals, including man.

In this specification the term "anorexia" is used to mean partial or complete loss of appetite, and this can have the beneficial effect of reducing weight, particularly in obese subjects.

It is known (U.S. Pat. No. 3,806,595) that 2-(o-ethoxyphenoxymethyl)morpholine, a compound which has antidepressant properties, also elicits a marked anorexiant effect in warm-blooded animals, including man. It is also known (U.S. Pat. No. 4,010,266) that certain optionally substituted 2-($\beta$-phenylvinyl)morpholine derivatives have antidepressant activity. It has now been discovered, and herein lies our invention, that one of the compounds disclosed in U.S. Pat. No. 4,010,266 has anorexiant activity in warm-blooded animals, and that this compound is surprisingly more potent, and has a much more rapid onset of action, than the compounds disclosed in U.S. Pat. No. 3,806,595.

According to our invention there is provided a method of producing anorexia in a warm-blooded animal in need of such an effect which comprises administering to the said animal an anorectically-effective amount of a compound selected from 2-($\beta$-phenyl-trans-vinyl)morpholine in the racemic form and the (2R) isomer thereof; and the non-toxic pharmaceutically-acceptable acid-addition salts thereof.

The optically active form of the compound used in the method of the invention is defined in terms of the absolute configuration at the asymmetric carbon atom 2 of the morpholine ring (the carbon atom, adjacent to the oxygen atom of the morpholine ring, through which the $\beta$-phenyl-trans-vinyl radical is attached) using the (R) and (S) system of nomenclature introduced by R. S. Cahn, C. K. Ingold and V. Prelog, Angew. Chem. Internat. Edn., 1966, 5, 385). The (2R) isomer of the compound used in the method of the invention, either as a solution of the free base in methanol or as a solution of the hydrochloride salt in water, produces a negative rotation in the plane of polarised light of the wavelength of the sodium D line.

The preferred compound for use in the method of the invention is (2R)-2-($\beta$-phenyl-trans-vinyl)morpholine and the non-toxic pharmaceutically-acceptable acid-addition salts thereof.

A suitable pharmaceutically-acceptable acid-addition salt of the morpholine derivative of the invention is, for example, a hydrochloride, phosphate or sulphate or an acetate, citrate, succinate or fumarate.

The method of the invention is particularly useful when applied to a man or woman, but it is also useful when applied to dogs, particularly obese dogs.

The anorexiant activity of the morpholine derivatives is most easily determined by measuring the food intake in rats or dogs.

The compound used in the method of the invention may be administered orally or parenterally, for example by intraperitoneal or intramuscular injection. In the case of a man or woman, the compound used in the method of the invention is most readily administered as a pharmaceutical composition in the form of a tablet or capsule. This formulation may be specially prepared, by methods well known to those skilled in the art, to permit sustained release. In the case of lower animals, for example the dog, the compound is most readily administered in admixture with the normal diet or in the form of a tablet or capsule.

When used in man or woman, a suitable regimen of administration is a total oral dose of 10 to 250 mg. per day of the compound (given in 1 to 3 doses per day) for 1 to 12 weeks and a preferred regimen is a single daily oral dose of 100 mg., preferably in a sustained release formulation, for 1 to 12 weeks.

When used in dogs, a suitable regimen of administration is a total dose of 10 to 250 mg. per day of the compound (given in 1 to 3 doses per day) for 1 to 12 weeks, and a preferred regimen is a single daily oral dose of 100 mg. for 1 to 12 weeks.

The invention is illustrated but not limited, by the following Examples:

EXAMPLE 1

Nine female beagle dogs fed an unrestricted meat diet in a regular 4 hour meal per day schedule were randomised into three groups of 3 dogs. The test compound was dosed orally as a dry solid in a standard soft gelatin capsule one hour before a weighed amount of food was supplied. Food consumption was measured after 1 hour, 2 hours and 4 hours, and the food was then removed. The dosing and feeding, using the above protocol, was continued for a further 4 days.

Using this test system, racemic 2-($\beta$-phenyl-trans-vinyl)morpholine hydrogen maleate, when dosed at 10 mg./kg., produced a mean reduction in food intake over hours 0–4 averaged over days 3–5 of 52%.

EXAMPLE 2

Female rats (> 220 g. in weight) were randomised by weight and grouped 3 to a cage prior to being adapted to inverted daylight conditions (12 hours light, 12 hours dark). Dry pelleted food was supplied from the beginning of the "night" for the next six hours and then withdrawn. After at least one week of training to this meal feeding schedule the test compound (ball-milled overnight in 0.5% aqueous Tween 80) was dosed by oral catheter to randomly selected groups (2 per treatment) one hour before food was supplied. Food intake during the first hour of the meal was measured and compared with 3 groups of controls dosed excipient.

Using this test system racemic 2-($\beta$-phenyl-trans-vinyl)morpholine hydrogen maleate when dosed at 50 mg./kg. produced a reduction in food intake compared with controls of 85%.

EXAMPLE 3

The experiment described in Example 1 was repeated using (2R)-2-($\beta$-phenyl-trans-vinyl)morpholine hydrochloride and it was found that this compound was 1.5 times as active as the corresponding racemate, that is it produced the same decrease in food consumption at two thirds of the dose.

EXAMPLE 4

A solution of racemic 2-($\beta$-phenyl-trans-vinyl)morpholine (63 g.) in hot ethanol (400 ml.) is added to a refluxing solution of (−)-O,O-dibenzoyltartaric acid monohydrate (31.36 g., 0.25 molar proportion) in ethanol (400 ml.) and the solution is allowed to cool slowly to 0° C. The resulting white solid of neutral dibenzoyltartaric acid salt (51.6 g.) is filtered off, 51.6 g., m.p. 158°–165° C. The filtrate is set aside.

The above solid is recrystallised from methanol (500 ml.) by cooling the solution to −20° C. to give a solid, 23 g., m.p. 178°–181° C., which is further recrystallised from solution in methanol (400 ml.) by cooling to −20° C. to give large colourless crystals, 14.9 g., m.p. 177°–181° C.

This recrystallised neutral dibenzoyltartaric acid salt is converted to the free base by stirring it in a mixture of 2N sodium hydroxide (100 ml.) and ether (150 ml.) until solution is complete. The layers are separated and the aqueous layer is saturated with sodium chloride and extracted with ethyl acetate (4 × 75 ml.). The ethyl acetate and ether phases are combined, dried by passing through a phase-separating paper and evaporated to dryness to give an oil which crystallises on standing (7.3 g.).

A portion of this residue (1 g.) is recrystallised from petroleum ether (b.p. 40°–60° C., 15 ml.) to form colourless rods of (−)-2-(β-phenyl-trans-vinyl)morpholine, 0.84 g., m.p. 65°–65.5° C., $[\alpha]_D^{25.5} -32.6°$ (c, 5 in methanol).

The remainder of the residue is converted to the hydrochloride by dissolving in ether and adding ethereal HCl. The resulting solid is recrystallised from isopropanol (100 ml.) to give (−)-2-(β-phenyl-trans-vinyl)morpholine hydrochloride, 6.5 g., m.p. 212°–213° C. (sealed tube), $[\alpha]_D^{24} -16.9°$ (c, 5 in water).

The filtrate from the precipitate of the neutral salt of the (−) isomer is concentrated to 500 ml. The quantity of (−)-O,O-dibenzoyltartaric acid monohydrate (65.1 g.) required to convert the free base in solution to the acid dibenzoyltartaric acid salt is dissolved in hot ethanol (200 ml.) and added to the concentrated filtrate. The solution is cooled to room temperature and the precipitate of the acid salt collected, 76.8 g., m.p. 161°–167° C.

The solid is recrystallised from hot ethanol (1500 ml.) 50.3 g., m.p. 159°–164° C., and again recrystallised from hot ethanol (1000 ml.), 32.6 g., m.p. 165°–169° C.

This recyrstallised salt is converted to the free base using the method described above to give a crystalline solid, 10.3 g. A portion (1 g.) is recrystallised from petroleum ether (b.p. 40°–60° C., 15 ml.) to give large colourless crystals of (+)-2-(β-phenyl-trans-vinyl)morpholine, 0.825 g., m.p. 64.5°–65° C., $[\alpha]_D^{25} +31.2°$ (c, 5 in methanol).

The hydrochloride of the remainder of the (+) isomer is prepared using the method described above for the (−) isomer. Recrystallisation from isopropanol (150 ml.) gives white crystals of (+)-2-(β-phenyl-trans-vinyl)morpholine hydrochloride, 9.3 g., m.p. 212°–213° C. (sealed tube), $[\alpha]_D^{24} +16.9°$ (c, 5 in water).

It was established that the (−) isomer had the (2R) configuration by relating it chemically to (2R)-4-benzyl-2-(toluene-p-sulphonyloxy)methylmorpholine (U.S. Pat. No. 3,973,158) whose absolute configuration had in turn been established by relating it chemically to (2R)-2-(o-ethoxyphenoxymethyl)morpholine (U.K. Pat. No. 1,427,097).

What we claim is:

1. A method of producing anorexia in a warm-blooded animal in need of such treatment which comprises orally or parenterally administering to said animal an anorectically-effective amount of a compound selected from the group consisting of 2-(β-phenyl-trans-vinyl)morpholine in the racemic form, the (2R) isomer thereof and the non-toxic pharmaceutically-acceptable acid-addition salts thereof.

2. A method as claimed in claim 1 in which the administered compound is (2R)-2-(β-phenyl-trans-vinyl)morpholine.

3. A method as claimed in claim 2 in which the warm-blooded animal is a man or woman.

4. A method as claimed in claim 2 in which the warm-blooded animal is a dog.

5. A method as claimed in claim 3 in which the man or woman is dosed with 10 to 250 mg. per day of the compound for a period of 1 to 12 weeks.

6. A method as claimed in claim 4 in which the dog is dosed with 10 to 250 mg. per day of the compound for a period of 1 to 12 weeks.

* * * * *